United States Patent [19]

Moriguchi

[11] Patent Number: 5,239,268
[45] Date of Patent: Aug. 24, 1993

[54] CONCRETE SENSOR FOR SENSING FRESH CONCRETE

[75] Inventor: Goro Moriguchi, Osaka, Japan

[73] Assignees: Asanuma Corp.; Universal System Control, Inc., both of Osaka, Japan

[21] Appl. No.: 900,606

[22] Filed: Jun. 18, 1992

[51] Int. Cl.$^5$ .............................. G01N 27/30
[52] U.S. Cl. .................. 324/425; 324/71.1; 324/693; 204/422
[58] Field of Search ............ 324/438, 439, 425, 71.1, 324/693; 204/412, 422, 423

[56] References Cited

U.S. PATENT DOCUMENTS

| | | | |
|---|---|---|---|
| 2,374,088 | 4/1945 | Fontana et al. | 324/439 |
| 2,606,748 | 8/1952 | Glegg | 324/693 X |
| 3,043,764 | 7/1962 | Harvey | 324/439 |
| 3,438,872 | 4/1969 | Johansson | 324/438 |
| 4,120,166 | 10/1978 | Brooks | 324/696 X |
| 4,927,503 | 5/1990 | Polly | 204/412 |
| 4,942,354 | 7/1990 | Miller | 204/153.1 |

FOREIGN PATENT DOCUMENTS 63-101823 6/1988 Japan.
1-1621 1/1989 Japan.

Primary Examiner—Kenneth A. Wieder
Assistant Examiner—Glenn W. Brown
Attorney, Agent, or Firm—Thompson, Hine and Flory

[57] ABSTRACT

A sensor for use during the construction of a concrete structure to enable an assessment to be made of whether or not a pour of fresh concrete has settled uniformly throughout the placement area. One of two main electrodes is fitted with an auxiliary electrode in parallel such that the polarity of the electrodes is reversed when they are immersed in water and when they are immersed in fresh concrete. By monitoring this function, it is possible to detect the presence or absence of fresh concrete in accordance with the polarity. In the case of a sensor without an auxiliary electrode, it is still possible to monitor changes in the voltage level when the electrodes are immersed in water and in fresh concrete, thereby providing access to a similar mode of assessment.

15 Claims, 8 Drawing Sheets

CONCRETE SENSOR FOR SENSING FRESH CONCRETE

BACKGROUND OF THE INVENTION:

1. Field of the Invention:

The invention relates to a sensor for the detection of slurries, such as freshly mixed concrete or mortar, containing cement constituents, said sensor being particularly well adapted to differentiate between such slurries and water.

2. Description of the Prior Art:

When building a concrete structure of any kind, it is common practice to pour the freshly mixed concrete in between sections of wooden formwork, for example, or else in between such wooden formwork and the face of the excavated area itself or the panel walling erected to cover it. Moreover, in order to ensure the quality of the concrete work, it is also important to take particular care to ascertain the state of the pour itself when carrying out the compaction work. Unfortunately, however, the various sheathing and stop end boards used to contain the wet concrete also effectively prevent the operator from carrying out a visual check of the pour or, at least, make it particularly difficult to do so. The conventional method of checking the quality of the pour has thus been for an operator of some years experience to simply tap the outside of the form and to assess the state of the concrete inside from the sound and the response it makes. In other words, in the final analysis, it is the skilled operator's instinct that plays the major role in assessing the quality of the work. Again, the traditional methods used to compact the concrete after pouring normally involve either striking the formwork with a wooden mallet in those areas which are adjudged, on the basis of tapping the outside of said formwork, to have already been filled with concrete, or else by shaking the whole of the formwork with vibrators or by dipping a stick vibrator with water in order to encourage the freshly mixed concrete to settle. If the operator's judgment proves misguided, however, then there is a danger that striking or shaking may end up damaging a part of the formwork which has not yet been filled and this may in turn become a source of defects in the completed concrete work.

Clearly, therefore, the application of the operator's experience or instinct to the assessment of the state of a pour in cases where visual checking is out of the question can only be an imperfect technique at best. An error in the initial assessment may, therefore, result in the subsequent compaction operation being carried out to little or no avail, thereby leaving the completed concreting work defective. One additional on-site problem is, of course, that although the work of concrete placement is particularly strenuous, it is nevertheless, for the reasons outlined above, not well suited to being carried out by young and inexperienced workers.

In recent years, therefore, techniques involving the use of electrical sensors in the assessment of the quality of concrete placement work have been disclosed in, for example, the Japanese Open Gazette 63 (1988) - 101823 and the Patent Gazette 64 (1989) - 1621. These techniques involve the use of a pair of electrodes, one fitted to each side of a piece of formwork into which freshly mixed concrete is subsequently poured. The sensor works by virtue of the fact that an electric current can then be passed between the electrodes using the moisture in the concrete as a conductor.

The problem with this method, however, is quite simply that the detection element that is being used by the sensor is, in fact, water and not the freshly mixed concrete itself.

In other words, the efficacy of the sensor rests on the fact that, since freshly mixed concrete contains an element of moisture, the detection of moisture is deemed to indicate the presence of concrete. Unfortunately, however, the degree of dependability of this method of detection is not by any means absolute.

When wooden formwork is being prepared to accept a placement of fresh concrete, for example, it is always rinsed very thoroughly with water first. The object of this exercise is first of all to clean the surface of the formwork and, at the same time, to moisten the inner surface of the formwork with water in order to prevent it from absorbing the water from the concrete itself, which would have the effect of reducing the moisture content of the fresh concrete and, in so doing, of impairing the setting process. It is also quite possible that excess water may collect on the formwork itself as a result of rainfall or of seepage from the face of the excavation. Thus, while it may be possible to place some faith in the results produced by this type of electrical sensor in cases where no water is used at all, the fact that water is almost invariably present for one reason or another renders the detection of water virtually meaningless as a means of determining the presence or absence of concrete.

Another problem which needs to be considered is typified by the case where concrete is to be poured to form the walls of a tunnel. There is currently no way of obtaining real-time confirmation of the quality of the pour at the crown of the tunnel. By positioning the concrete sensor of the invention close to the crown of the tunnel in advance of the pour and then pouring the concrete, however, the quality of the pour can be confirmed electrically, thereby avoiding the risk of weakness that could result from an unsatisfactory pour.

SUMMARY OF THE INVENTION

The present invention completely eliminates all the problems attendant on the use of the conventional working methods outlined above. It is, therefore, the primary object of this invention to provide a concrete sensor which is capable of detecting the presence of fresh concrete by making a clear distinction in operation between water and fresh concrete.

It is another object of the invention to provide a combination of metals which is perfectly suited for use in electrodes designed to detect the presence of concrete.

It is a further object of the invention to provide a means of applying the effectiveness of the invention in the detection of concrete to the prevention of other problems, such as the incidence of cavities in the walls and slabs of concrete structures.

The first essential design feature of the concrete sensor of the invention involves the fitting of an auxiliary electrode in parallel with the first of the two main electrodes and in the running of a lead wire from the point at which the first main electrode and its auxiliary electrode meet, while at the same time running a separate lead wire from the second main electrode. At the same time, the electrodes themselves are also made from a combination of metals which is designed to ensure that the polarity generated in the two lead wires is reversed when the electrodes are immersed in water from that which is exhibited when they are immersed in fresh concrete.

The second essential design feature of the invention involves the connection to the first main electrode of an auxiliary electrode of almost the same surface area as said first main electrode, a lead wire being run from said auxiliary electrode and a separate lead being run from the second main electrode. The combination of metals used to make the electrodes then ensures that the polarity generated in these two lead wires is reversed when the electrodes are immersed in water from that which is exhibited when they are immersed in fresh concrete.

It is also the inventors' intention to disclose a technique for the combination of the metals used to make the electrodes of the concrete sensor of the invention whereby the immersion of said concrete sensor, in which a separate lead wire has been run from each of said electrodes, in either water or fresh concrete produces not a reversal of the polarity generated in said lead wires but, rather, a change in the voltage generated between the electrodes. The objects, special features and benefits of the present invention may be clarified by reference to the following detailed description of the invention and the accompanying drawings.

DESCRIPTION OF THE PREFERRED EMBODIMENTS

Figure 1:
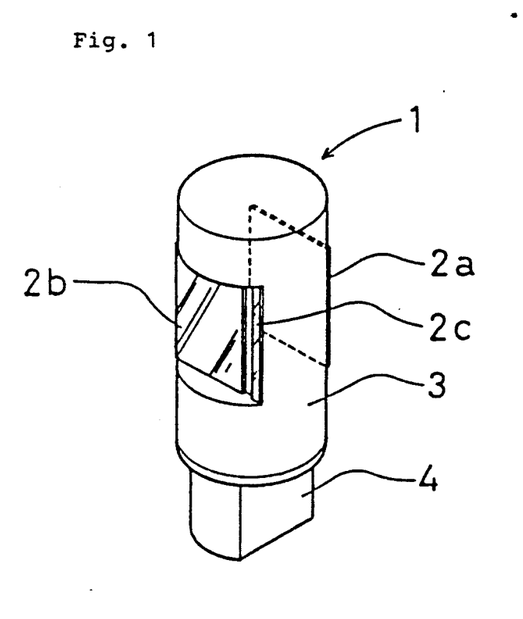
FIG. 1 shows an oblique view of one preferred embodiment of the kind of structure used in the concrete sensor of the invention.

There follows a description of the preferred embodiments of the invention by reference to the accompanying drawings. FIG. 1 shows one of the preferred embodiments of the concrete sensor 1 in which 2a is the first main electrode, 2b is the second main electrode and 2c is an auxiliary electrode that is connected electrically to the second main electrode 2b. 3 is a housing made of an insulating material and 4 is a socket which serves both to secure the concrete sensor 1 and, at the same time, to connect it electrically to the detection device described below. Two lead wires, one from each of said main electrodes, are run out through the bottom of said socket 4 to form a pair of terminals. A plurality of said concrete sensors 1 are fixed in strategic positions around the formwork into which the fresh concrete is due to be poured. Subsequently, when the concrete is actually poured into the formwork, a voltage is generated in each of said concrete sensors 1 and this is detected and the required diagnosis carried out.

Figure 2:
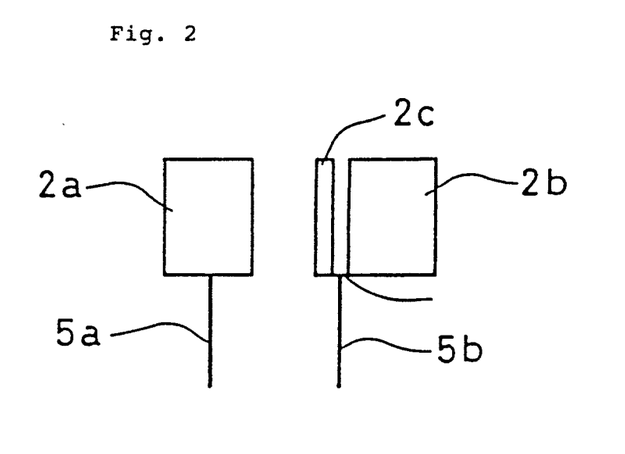
FIG. 2 shows a typical example of one of the electrodes used in the concrete sensor of the invention.

FIG. 2 illustrates the typical relationship which exists between the two main electrodes 2a, 2b of the concrete sensor 1 and the auxiliary electrode 2c. A lead 5a runs from the first main electrode 2a and a second lead 5b runs from the contact point 6 of the second main electrode 2b and the auxiliary electrode 2c, each of said pair of leads being connected to metal terminal fittings in the aforementioned socked 4. Each of the two main electrodes 2a, 2b and the auxiliary electrode 2c is, moreover, made of a different kind of metal (three different metals in all). There is, of course, a large number of different combinations of metals that could be chosen and, for the purposes of the following description, we have opted for zinc for the first main electrode 2a, aluminium for the second main electrode 2b and tin for the auxiliary electrode 2c.

After electrically insulating the second main electrode 2b and the auxiliary electrode 2c from each other, the concrete sensor 1 was first immersed in neutral water with a pH of 7. The electromotive force generated between each of the electrodes was then measured and found to be 0.5 V between the tin auxiliary electrode 2c, which registered positive polarity, and the zinc first main electrode 2a, which registered negative polarity. At this time, the surface area of the two main electrodes 2a, 2b was approximately 3 square cm each while that of the auxiliary electrode 2c was about 1/10 of that size. It as also observed that there was no electromotive force generated between the zinc electrode 2a and the aluminium electrode 2b. Next, the aluminium electrode 2b and the auxiliary electrode 2c were connected electrically by way of the contact point 6 and the lead 5b run out to form the basic concrete sensor 1. Readings were then taken between the two leads 5a, 5b and again a voltage of 0.5 V was detected with lead 5a registering negative polarity and lead 5b registering positive polarity.

The same concrete sensor 1 was then immersed in an alkaline solution (pH of about 13) of freshly mixed concrete and measurements taken of the electromotive force that was generated. On this occasion, the polarity of both the zinc electrode 2a and the tin auxiliary electrode 2c were found to be the same as when the sensor was immersed in water with an electromotive force of approximately 0.3 V being generated between the zinc electrode 2a, which registered negative polarity, and the auxiliary electrode 2c, which registered positive polarity. An electromotive force of 0.8 V was also measured between the zinc electrode 2a and the aluminium electrode 2b with said zinc electrode 2a registering positive polarity and said aluminium electrode 2b registering negative polarity. Again, just as in the case of the immersion in water, the aluminium electrode 2b and the auxiliary electrode 2c were connected to unify them electrically, and the voltage arising between the lead 5b running from the two combined electrodes 2b, 2c and the lead 5a running from the zinc electrode 2a was measured and again found to be 0.5 V. The polarity of the two lead wires was, however, found to have been reversed with lead 5a now exhibiting positive polarity and lead 5b now exhibiting negative polarity. The reason for this reading is to be found in the electrical shorting between the aluminium electrode 2b and the auxiliary electrode 2c which results in a canceling out of the opposing voltages through the contact point 6, thereby effectively combining the voltage values of the aluminium electrode 2b (negative 0.8 V) and the auxiliary electrode 2c (positive 0.3 V).

It is also worth noting in passing that, when the concrete sensor 1 was immersed in a dilute solution of hydrochloric acid with a pH of about 3, the polarity of the two leads 5a,5b remained the same as during immersion in water with the electromotive force being measured at approximately 0.2 V.

From the above, it can be seen that, although the absolute value of the voltage generated between the two leads 5a,5b of the concrete sensor 1 illustrated in FIG. 1 and FIG. 2 remains the same whether said sensor 1 is immersed in neutral water or in an alkaline solution of freshly mixed concrete, the polarity is, on the other hand, reversed. This is thought to reflect both the pH value of the solution in which the sensor 1 is immersed and also the ionization tendency of the three different metals used. Thus, if the voltage generated in the concrete sensor 1 is input to a detection device in the form of an electric circuit connected further downstream, the polarity will be different in the case of water to that which is exhibited in the case of fresh concrete and the detector circuit can, therefore, be designed to be activated in the case of water and not in the case of concrete or vice versa, whichever is preferred. In other words, since all that needs to be determined is the polarity, the readings provided are extremely clear cut. Moreover, the growing problem of acid rain is unlikely to adversely affect the readings provided by the sensor since the polarity of an acid solution was found to be the same as that of neutral water.

For the purposes of the description of the present preferred embodiment, moreover, the first main electrode 2a has been assumed to be made entirely of zinc and the auxiliary electrode 2c has been assumed to be made entirely of tin. These electrodes would be equally effective, however, if only their surfaces consisted of zinc and tin respectively with the result that galvanized iron sheet could equally well be used in place of the zinc electrode 2a while tin plate could similarly be used for the auxiliary electrode 2c. One way or another, the present invention includes all possible combinations of metals which result in a reversal of the polarity of the current generated in the lead wires when the invention is immersed in water and when it is immersed in freshly mixed concrete.

Furthermore, in the event that the concrete sensor 1 of the invention is cut off from the freshly mixed concrete after it has been immersed in said concrete, the electromotive force will change. In other words, although, when immersed in fresh concrete, an electromotive force of 0.5 V is generated between the positive lead 5a and the negative lead 5b, the removal of the sensor 1 from the concrete will result, after a fixed period of time has elapsed, in a reversal of the polarity of said lead wires 5a,5b which will then display the same polarity as when the sensor is dipped in water. This happens because, when the sensor is first removed from the wet concrete, a certain amount of alkaline solution remains attached to the sensor and this continues to react chemically with the sensor in the same way as when the sensor was immersed in the concrete. However, since the amount of said alkaline solution is also limited, said chemical reaction also reaches saturation point with the passage of time and the sensor then reverts to the stable state characteristic of periods of immersion in neutral water. The length of time required for the polarity to change depends on the ratio of the surface areas of the aluminium electrode 2b and the auxiliary electrode 2c. To be more precise, although the voltage remains unchanged, the bigger the surface area of the auxiliary electrode 2c, the greater the tendency to diminish the electromotive force of the aluminium electrode 2b and the zinc electrode 2a and this in turn reduces the amount of time required for the chemical reaction to reach it saturation point. It is thus possible to set the response time to any required value simply by adjusting the surface area of the auxiliary electrode 2c. Providing an area is fitted with a concrete sensor, therefore, it will be possible for said sensor to accurately detect a subsequent loss of concrete for any reason from said area after the initial pouring of fresh concrete.

Figure 3:
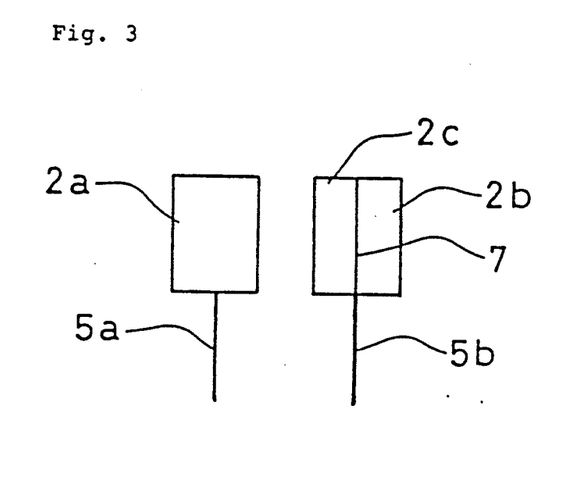
FIG. 3 shows an example of another type of electrode.

FIG. 3 shows an alternative preferred embodiment of the electrodes of the invention. In this embodiment, the zinc electrode 2a remains unchanged from that described in connection with the first preferred embodiment above. The surface areas of the aluminium electrode 2b and the auxiliary tin electrode 2c have, however, been made roughly equal with the lead wire 5b being run out from whichever part of the auxiliary electrode 2c is preferred. While bonding of the lead 5b with aluminium is difficult, the bonding of said lead 5b with tin is comparatively easy. In this case, although there is electrical short circuiting along the boundary line 7 between the aluminium electrode 2b and the auxiliary electrode 2c, the relationship between them in terms of the electromotive force generated remains the same as that described in connection with the first preferred embodiment above. The comparative surface area of the auxiliary electrode 2c was increased above that of the first preferred embodiment in deference to the need to negate the effect of the aluminium electrode 2b on the tin auxiliary electrode 2c when immersed in water. In the present case, the setting of the time required for polarity to revert to its original state, in the event that the contact with fresh concrete is curtailed for any reason, can again be carried out by adjusting the ratio of the surface areas of the aluminium electrode 2b and the auxiliary electrode 2c.

Furthermore, if the metal used for the auxiliary electrode 2c, for example, is changed from tin to lead, there is virtually no difference in the results achieved from those outlined above. This is because the ionization tendencies of tin and lead are not only adjacent in the series of ionization tendencies but also approach each other very closely.

Since the design of the present preferred embodiment calls both for the joining of the second main electrode with the auxiliary electrode and also for an increase in the size of the auxiliary electrode until its surface area roughly equals that of the second main electrode, this effectively also doubles the surface area of said second main electrode. Moreover, since half the electrode area is now accounted for by the auxiliary electrode, this requirement can easily be satisfied with the help of a plated metal. Not only is the performance of this sensor unchanged from that described in connection with the first preferred embodiment above, it is also very cost effective and this in turn makes it particularly suitable for mass production.

The third preferred embodiment of the invention dispenses entirely with the use of an auxiliary electrode and utilizes just a single pair of electrodes. In this embodiment, a copper electrode and an aluminium electrode, each with an effective surface area of 2 square cm, were used. When this sensor was immersed in water, the copper electrode displayed positive polarity and the aluminium electrode displayed negative polarity, with the electromotive force being measured at 0.45 V. When the sensor was immersed in wet concrete, on the other hand, the polarity remained unchanged but the measured electromotive force increased to 1.10 V. In the case of the present embodiment, the polarity in the lead wires is not reversed but, if a value such as 0.6 V is selected as the "threshold value" and the leads are then connected to a detection circuit which is activated only by a current which exceeds said threshold value, then it again becomes a simple matter to tell whether the medium in which the concrete sensor has been immersed is either water or fresh concrete. Moreover, the choice of metals used for the two electrodes is not confined to copper and aluminium, and any combination of metals which gives rise to sufficiently different electromotive forces to enable a clear distinction to be made between immersion in water and immersion in concrete may, therefore, be considered to fall within the scope of the present invention.

The fact that the third preferred embodiment does not call for the use of an auxiliary electrode also makes it easy to put together. Moreover, since the difference between the electromotive forces produced by immersion in water and in wet concrete is large, it is also a comparatively easy matter to set the "threshold value" required to distinguish between the two.

Figure 4:
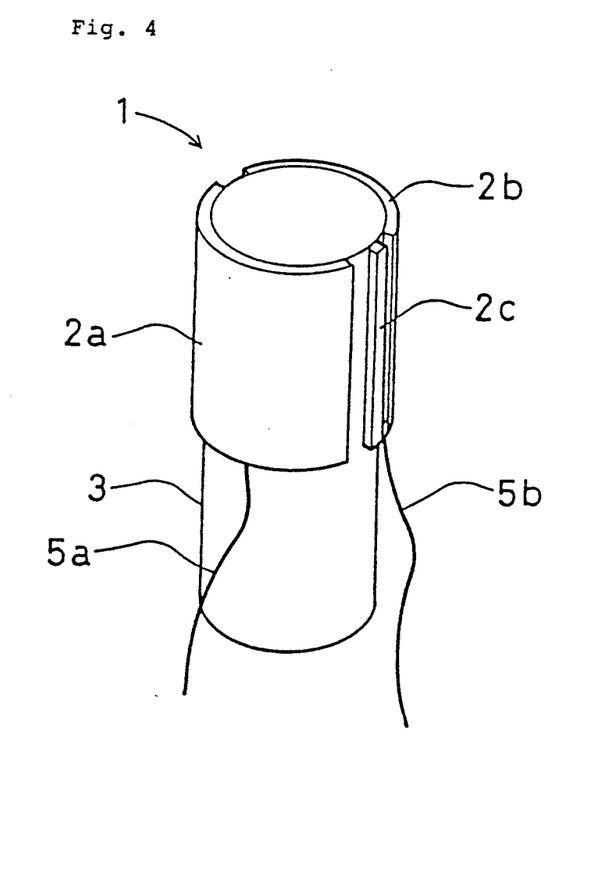
FIG. 4 is an oblique view of a different shape of the concrete sensor of the invention.
Figure 5:
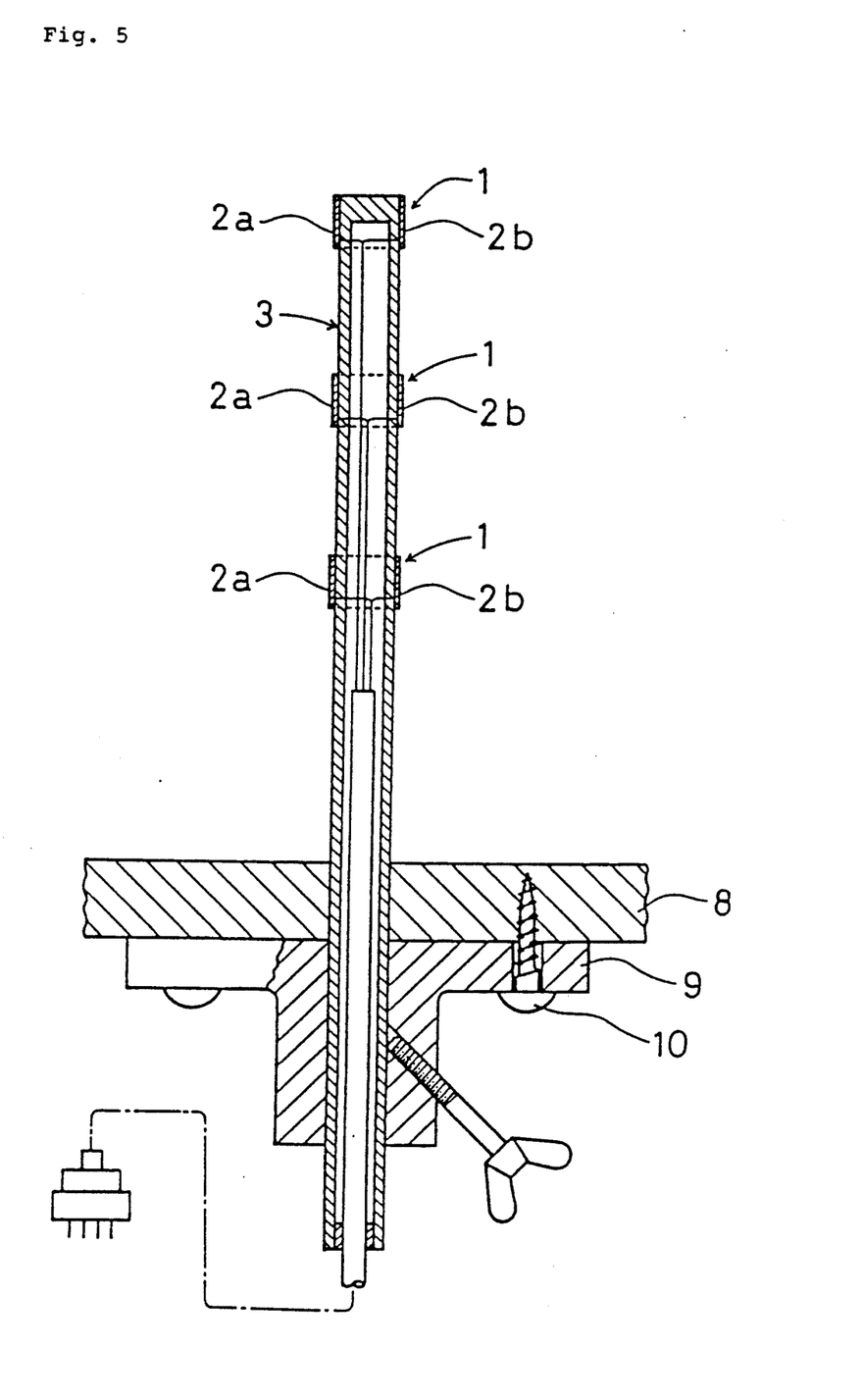
FIG. 5 is a cross sectional view showing the arrangement in sequence of a plurality of concrete sensors having the different shape shown in FIG. 4.

FIG. 4 illustrates a concrete sensor of a different shape. In order to keep the explanation as simple as possible, we have labeled parts which have a similar function to the comparable part in FIG. 1 with the same numbers. The main point to note is that the two main electrodes 2a,2b and the auxiliary electrode 2c have been positioned in this case on the outside of the insulated housing 3. The adoption of this type of design enables the housing 3 itself to be elongated, as shown in FIG. 5, into the form of a cylinder to which electrodes can then be fitted at suitable intervals and the leads from each electrode run into the interior of said housing 3. This in turn enables the creation of a sort of rod shaped sensor on which a plurality of individual concrete sensors are located at suitable intervals. In FIG. 5, 8 is the formwork which will hold the poured concrete, 9 is a fitting used to secure the sensor to said formwork and 10 is a retaining screw to secure said fitting 9 to said formwork 8.

Figure 6:
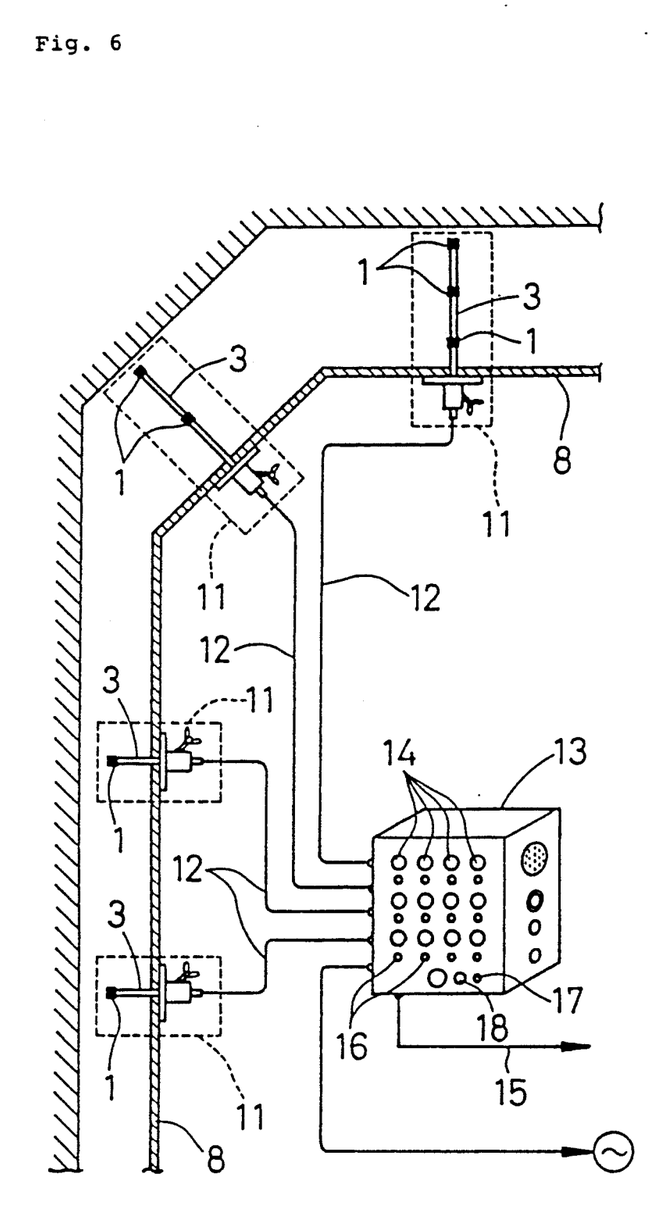
FIG. 6 is a schematic representation of the concrete sensor of shown in FIG. 5 fitted to formwork used for the placement of concrete.

In order to detect the presence of fresh concrete using the concrete sensor of the present preferred embodiment, a device of the type shown in FIG. 6 is required. The elements labeled 11, each of which is enclosed by dotted lines in the drawing, are rod sensors of the type illustrated in FIG. 5 and are fitted to the formwork 8 at appropriate intervals. The detection signals are input by each of the detection output cables 12 to a detection device 13 which then determines the individual detection status of each of the concrete sensors. The detection device 13 itself is equipped with indicator lamps 14, which display the operating status of each of the individual concrete sensors, a communication cable 15, which enables the external output of said operating statuses, test buttons 16, which are used to check the concrete sensors and other fittings such as a power supply switch 17 and a power indicator lamp 18.

Figure 7:
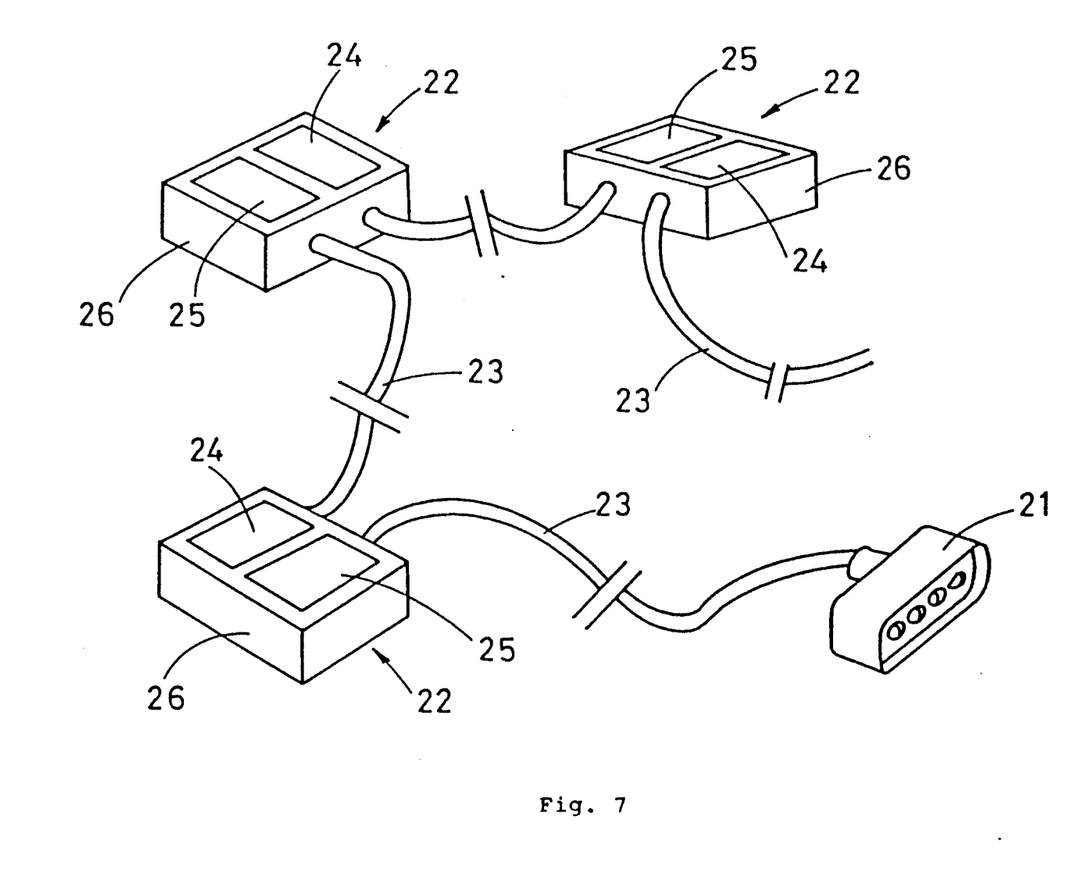
FIG. 7 shows a different embodiment of the invention in which a plurality of concrete sensors are connected in series.
Figure 8:
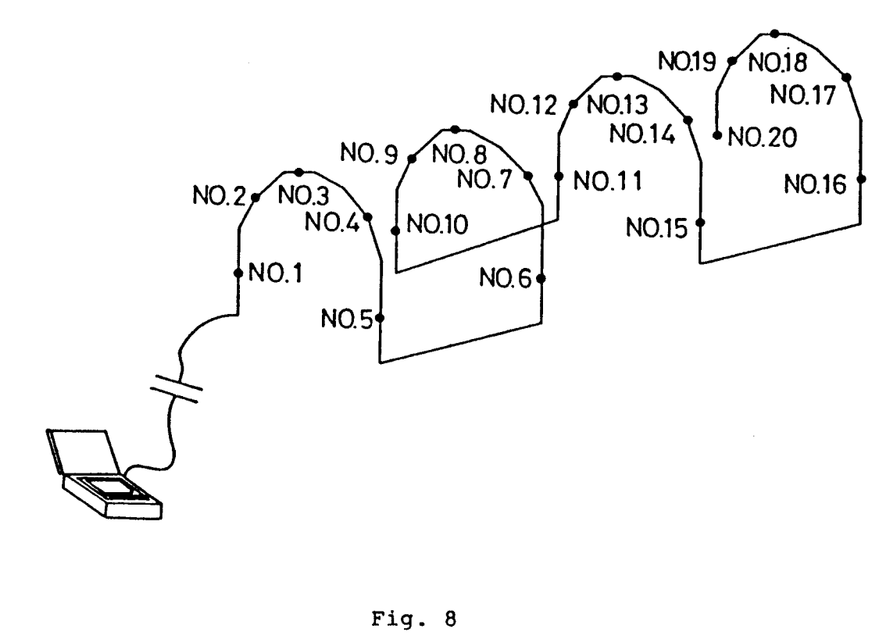
FIG. 8 is a diagram illustrating the arrangement of a plurality of concrete sensors of the type shown in FIG. 7 in readiness for the placement of concrete during the construction of a tunnel.
Figure 9:
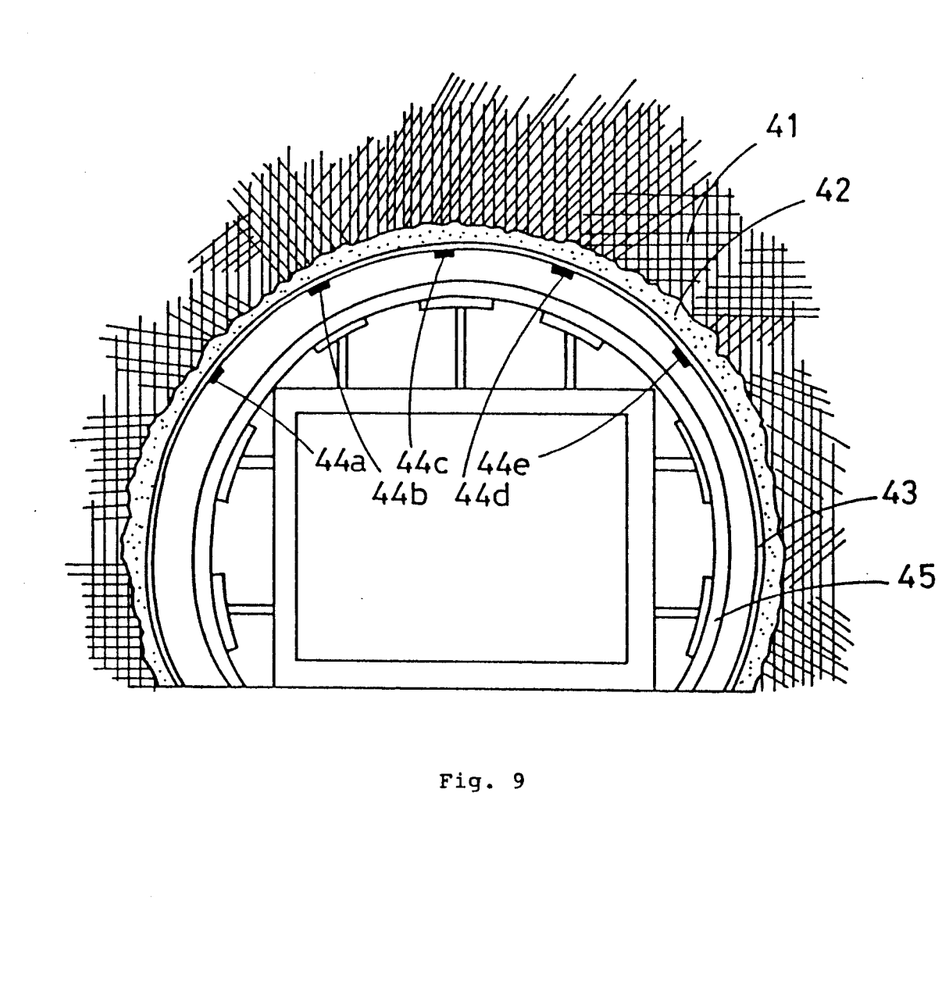
FIG. 9 is a cross sectional view of the tunnel.
Figure 10:
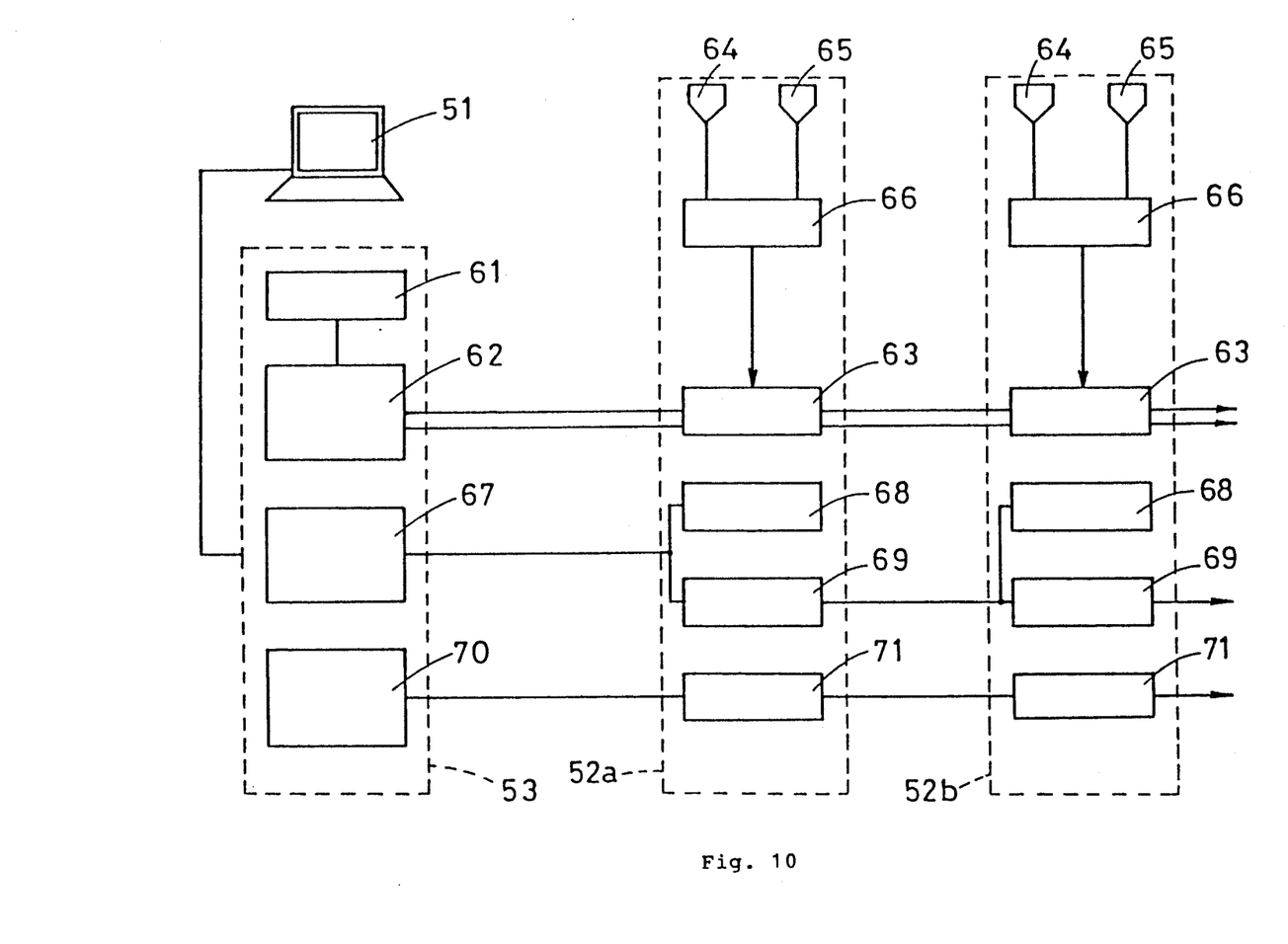
FIG. 10 is a block diagram illustrating the method of centralized control by computer of the sensors shown in FIG. 7 and FIG. 8.

FIG. 7 is an oblique view of a plurality of the concrete sensors of the present invention connected in series to each other and then to the input/output terminal of a control device of some kind, such as a computer. In the drawing, 21 is a connector for connection to a control device, 22 are each concrete sensors and 23 is the cable by means of which each of said concrete sensors 22 is connected in series. Although the concrete sensors of the present embodiment each have a pair of electrodes 24,25 fitted to the surface of the housing 26, it would, of course, be equally acceptable to replace said sensors with concrete sensors of the type which also incorporate an auxiliary electrode. The concrete sensors are in this case arranged in series quite simply to eliminate the troublesome wiring work involved in connecting sensors to the control device in parallel. FIG. 8 illustrates the practical application of concrete sensors connected in series, as shown in FIG. 7, in readiness for the placement of concrete during the construction of a tunnel. There are 20 connected sensors in all numbered from No.1 to No.20 in the drawing. The concrete sensors themselves are grouped in sets of five with each set being arranged around the cross-sectional line of the tunnel. The sensors have been arranged in sets of five purely for the purposes of illustration and could, of course, be arranged in sets of any number as preferred. 31 is the control device for which a portable computer would normally be used, the status of each concrete sensor being displayed individually on the monitor screen. Normally, the bare rood and walls 41 of the tunnel are first sprayed with a thin coating of concrete 42 which is then covered by a waterproof sheet 43. The concrete sensors 44a–44e themselves are then fitted as shown in FIG. 9. 45 is the form for tunnel lining. When the fresh concrete is placed, it tends, of course, to settle downwards and there is generally speaking little problem with the pour in the lower part of the tunnel. Any defects in the pour are normally located in the upper part and, for this reason, the sensors too are concentrated in the upper area as shown in the drawing. FIG. 10 is a block diagram which illustrates the communication technique required for the centralized control by a control device of a plurality of concrete sensors connected in series. In the drawing, 51 is the control device, the blocks 52a, 52b marked by the dotted lines are each concrete sensors while block 53 is an interface between said control device 51 and said concrete sensors 52a,52b. Power is supplied in parallel to each of the concrete sensors from a 24 V concrete sensor power supply 61 located in the interface 53. 62 is a voltage drop detection means which is used to detect any drop in the voltage of the power supply section 63 of each concrete sensor. 64 and 65 are each concrete sensor electrodes, the configuration as shown being treated as including the case where one of said electrodes 64,65 also comprises an auxiliary electrode. 66 is a circuit which detects the voltages generated by said electrodes 64,65. Since, in the present embodiment, the concrete sensors are connected in series, the detection of the output of each individual sensor calls for sequence control. 67 is a sequence control circuit, which is incorporated into the aforementioned interface 53, and 68 and 69 are control circuits and bypass circuits respectively, each concrete sensor being provided with one of each. These circuits 67,68,69 together comprise the means by which the sequencing function is controlled. On receipt of the first control pulse transmitted from the sequence control circuit 67, the control circuit 68 of the first concrete sensor activates its communication section. If said sensor detects the presence of fresh concrete then its detection circuit 66 will determine that a voltage has been generated between the electrodes 64,65 and it will then cause the voltage of the power supply 63 to drop for a fixed period of time. If, on the other hand, the sensor does not detect the presence of fresh concrete, then it will not cause the power supply voltage to drop. The voltage drop detection means 62, which is incorporated into the aforementioned interface 53, will now detect the drop in voltage and display this information in the display area of the control device 51. At the same time, when the first concrete sensor has transmitted its detection signal, it immediately activates its bypass circuit 69 and suspends its communication function until such time as it receives a reset signal from the interface 53. The time required by the first concrete sensor from receipt of the control pulse through to activation of its bypass circuit 69 is extremely short and if set to, say, something in the region of 5/10,000 of a second, this enables readings to be taken from as many as 100 separate sensors in a very short time. When the second control pulse is sent out, the first concrete sensor will not respond since its communication function has been suspended. As a result, the second control pulse is routed along the first concrete sensor's bypass circuit and eventually received by the control circuit of the second concrete sensor where a similar series of operations to those outlined above in respect of the first concrete sensor is carried out. Concrete sensors connected in series are controlled in this way. It would also be possible to enter the total number of connected sensors into the control device 51 in advance such that a reset signal could be transmitted as soon as the detection signal from the last concrete sensor had been received. This would enable all the concrete sensors to be reset at the same time, thereby enabling the whole detection process to start again from the beginning. 70 is a test control circuit which is connected in series to test circuits 71 incorporated into each of the concrete sensors. When this circuit is set, each of said concrete sensors outputs a detection signal, thereby enabling the detection function to be checked.

What is claimed is:

1. A concrete sensor comprising:
   first and second main electrodes, said second main electrode having an auxiliary electrode oriented parallel thereto, said first, second and auxiliary electrodes each having a contact point thereon;
   a single lead wire extending from both of said contact points of said second main electrode and said auxiliary electrode;
   said first main electrode having a single lead wire extending from said contact point thereon; and
   said electrode being composed of a metallic material having a polarity of a voltage generated in said two lead wires which varies depending on whether said electrodes are immersed in water or in fresh concrete.

2. The concrete sensor according to claim 1 in which one of the main electrodes is made of aluminium, the auxiliary electrode is made of tin and the other main electrode is made of zinc.

3. The concrete sensor according to claim 2 in which the auxiliary electrode made of tin is replaced by an auxiliary electrode made of lead.

4. The concrete sensor according to claim 1 in which one of the main electrodes is made of aluminium, the auxiliary electrode is made of tin plate and the other main electrode is made of galvanized iron sheet.

5. The concrete sensor according to claim 1 in which the two main electrodes each have a surface area of approximately 3 square centimeters and the auxiliary electrode has a surface area of 1/10 of that value.

6. The concrete sensor according to claim 1 in which a plurality of concrete sensors are connected in series.

7. A concrete sensor comprising two main electrodes, the first of which is connected to an auxiliary electrode of almost the same surface area, a single lead wire extending from said auxiliary electrode and another single lead wire extending from the second main electrode, said electrodes comprising a combination of metals that is conducive to a reversal in the polarity of a voltage generated in said two lead wires depending on whether said electrodes are immersed in water or in fresh concrete.

8. The concrete sensor according to claim 7 in which one of the main electrodes is made of aluminium, the auxiliary electrode is made of tin and the other main electrode is made of zinc.

9. The concrete sensor according to claim 8 in which the auxiliary electrode made of tin is replaced by an auxiliary electrode made of lead.

10. The concrete sensor according to claim 7 in which one of the main electrodes has a surface area twice that of the other main electrode, half of the larger electrode being made of a plated metal and used as an auxiliary electrode.

11. The concrete sensor according to claim 10 in which the auxiliary electrode made of tin is replaced by an auxiliary electrode made of lead.

12. The concrete sensor according to claim 7 in which a plurality of concrete sensors are connected in series.

13. A concrete sensor for detecting fresh concrete comprising:
    lead wires extending from two electrodes;
    said electrodes being made of a combination of metals that is conducive to the generation of a first voltage less than a threshold value in said two lead wires when said electrodes are immersed in water and generation of a second voltage greater than said threshold value when said electrodes are immersed in fresh concrete; and
    a voltage detection circuit connection to said lead wires activated only when said second voltage exceeds said threshold value.

14. The concrete sensor according to claim 13 in which one of the electrodes is made of aluminium and the other electrode is made of copper.

15. The concrete sensor according to claim 10 in which a plurality of concrete sensors are connected in series.

* * * * *